US00PP33945P2

(12) United States Plant Patent
Ranney et al.

(10) Patent No.: US PP33,945 P2
(45) Date of Patent: Feb. 8, 2022

(54) AZALEA PLANT NAMED 'NCRX6'

(50) Latin Name: ***Rhododendron* hybrid**
Varietal Denomination: NCRX6

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 17/343,144

(22) Filed: Jun. 9, 2021

(51) Int. Cl.
*A01H 6/38* (2018.01)
*A01H 5/00* (2018.01)

(52) U.S. Cl.
USPC ..... Plt./240

(58) Field of Classification Search
USPC ..... Plt./240
See application file for complete search history.

*Primary Examiner* — Annette H Para
(74) *Attorney, Agent, or Firm* — Cassandra Bright

(57) ABSTRACT

A new and distinct cultivar of *Rhododendron* plant named 'NCRX6' having a profusion of bright red/orange single flowers, cold-hardiness to USDA 6b, consistent Fall reblooming, a dense habit, and tetraploid cytotype. Plants exhibit mid-sized habit and propagate readily from stem cuttings. The new cultivar is a *Rhododendron*, suitable for ornamental garden purposes.

2 Drawing Sheets

Latin name of the genus and species: The Latin name of the novel plant variety disclosed herein is *Rhododendron* hybrid.

Variety denomination: 'NCRX6'.

The inventive hybrid was selected from oryzalin-treated seedlings derived from a controlled cross between evergreen azaleas 'Fourth of July' (unpatented, female) and 'Girard's Caroline' (unpatented, male). Prior to the designation of the varietal denomination, 'NCRX6' was referred to by its experimental code: H2009-271-001. 'NCRX6' is a stable tetraploid cytotype.

BACKGROUND OF THE INVENTION

The present invention comprises a new and distinct hybrid evergreen azalea cultivar hereinafter referred to by the cultivar name 'NCRX6'. This hybrid azalea was developed by a controlled breeding program at North Carolina State University, in Mills River, N.C. 'NCRX6' was selected for its profusion of vivid red/orange single flowers, moderate and dense growth habit, and consistent Fall reblooming. 'NCRX6' was obtained from the controlled, hand pollination of emasculated *Rhododendron oldhamii* 'Fourth of July' (unpatented) and male/pollen parent *Rhododendron* 'Girard's Caroline' (unpatented). Seedlings from these controlled pollinations were then treated with a mitotic inhibitor (oryzalin) to develop a population of stable tetraploid azaleas. 'NCRX6' was selected from this population after 8 years in container and field trials at the Mountain Horticultural Crops Research and Extension Center in Mills River, N.C. Container trials were conducted using pine bark media supplemented with 1.04 $kg \cdot m^{-3}$ dolomitic lime, 0.74 $kg \cdot m^{-3}$ granulated micronutrients (Micromax; ICL Specialty Fertilizers, Tel Aviv, Israel) and top-dressed with 5- to 6-month slow-release fertilizer (Osmocote Plus 15-9-12, ICL Specialty Fertilizers). Full-sun field trials were conducted in plastic-covered, bark-amended clay soils with minimum winter temperatures of −2° F. (−19° C.) and maximum summer temperatures 98° F. (37° C.). The first asexual propagation of 'NCRX6' occurred in 2011 by rooting stem cuttings at the North Carolina State University Mountain Horticultural Crops Research Station, Mills River, N.C. 'NCRX6' roots readily from firm softwood cuttings treated with a basal dip of 3,000-5,000 ppm indole-3-butyric acid (potassium salt) in water. 'NCRX6' has been found to retain its distinctive characteristics through successive asexual propagations over 10 years.

Genome size and ploidy level were determined via flow cytometry, following the methods described in Jones et al., 2007, using the internal standard *Pisum sativum* 'Ctirad' and DAPI (4',6-Diamidino2-phenylindole)fluorochrome. 'NCRX6' was found to have a genome size of approximately 2.6 pg indicating a tetraploid cytotype. This is approximately two times the size of diploid cytotypes. *Ploidy levels and relative genome sizes of diverse species, hybrids, and cultivars of rhododendron*. Journal of the Amerierican *Rhododendron* Society 61(4):220-227. Jones, J. R., T. G. Ranney, N. P. Lynch, and S. L. Krebs. 2007.

SUMMARY OF THE INVENTION

The following are the unique combination of characteristics of this new cultivar when grown under standard horticultural practices at North Carolina State University, Mountain Horticultural Crops Research Station, Mills River, N.C.

1. Profusion of vivid orange/red single flowers.
2. Cold hardiness to USDA Zone 6b.
3. Compact habit.
4. Consistent Fall reblooming.
5. Tetraploid cytotype.

COMPARISON WITH PARENTS

TABLE 1

| Plant | Flower Color | Flower Type | Habit |
|---|---|---|---|
| FEMALE: *Rhododendron oldhamii* 'Fourth of July' (unpatented) | Red RHS Red Group 39A | Single | Hardiness: USDA Zone 7B. Mature Height × Width: 250-300 cm × 180-200 cm. Ploidy: Diploid. Flower size: 4-6 cm. |
| MALE: *Rhododendron* 'Girard's Caroline' (unpatented) | Dark rose | Single | Hardiness: USDA Zone 6B. Mature Height × Width: 90 × 120 cm. Ploidy: Diploid. |
| *Rhododendron* 'NCRX6' | Red RHS Red Group 42A. | Single | Hardiness: USDA Zone 6B. Mature Height × Width: 75 × 90-120 cm. Ploidy: Tetraploid. Flower size: 4.5-6.5 cm. |

COMPARISON WITH COMMERCIAL CONTROLS

TABLE 2

| Plant | Flower Color and Type | Habit | Additional characteristics |
|---|---|---|---|
| *Rhododendron* 'Roblez' U.S. Plant Pat. No. 28,279 P3 | Red, semi-double flowers, lacking additional petaloids, smooth hose-in-hose flower appearance RHS Red Group 53B. | Compact: 75 cm × 90 cm | Hardy to Zone 6 |
| *Rhododendron* 'Conlen' U.S. Plant Pat. No. 11,628 P | Red, single/semi-double flowers with some petaloids. RHS Red Group 46B. | Mid-sized/ large 120-150 × 120-150 cm | Hardy to Zone 7 |
| *Rhododendron* 'Conleb' U.S. Plant Pat. No. 10,581 | Red single to semi-double flowers with some petaloids RHS Red Group 44A. | Mid-sized/ large 120 × 140 cm | Hardy to Zone 7 |
| *Rhododendron* 'Conleo' U.S. Plant Pat. No. 11,640 | Red/salmon semi-double flower with some petaloids RHS Red Group 44D | Mid-sized, large 150-180 × 150-180 cm | Hardy to Zone 7 |
| *Rhododendron* 'NCRX6' | Red/orange single flowers; dense habit; few to no petaloids. RHS Red Group 43A. | Mid-sized/ compact 75 × 90-120 cm | Hardy to Zone 6b |

BRIEF DESCRIPTION OF THE DRAWINGS

'NCRX6' is illustrated by the accompanying photographs, which show the plant's form, foliage, and inflorescences. The colors shown are as true as can be reasonably obtained by conventional photographic procedures. Colors in the photographs may differ slightly from the color values cited in the detailed botanical description, which accurately describe the new hybrid *Rhododendron.*

DETAILED BOTANICAL DESCRIPTION

Figure 1:
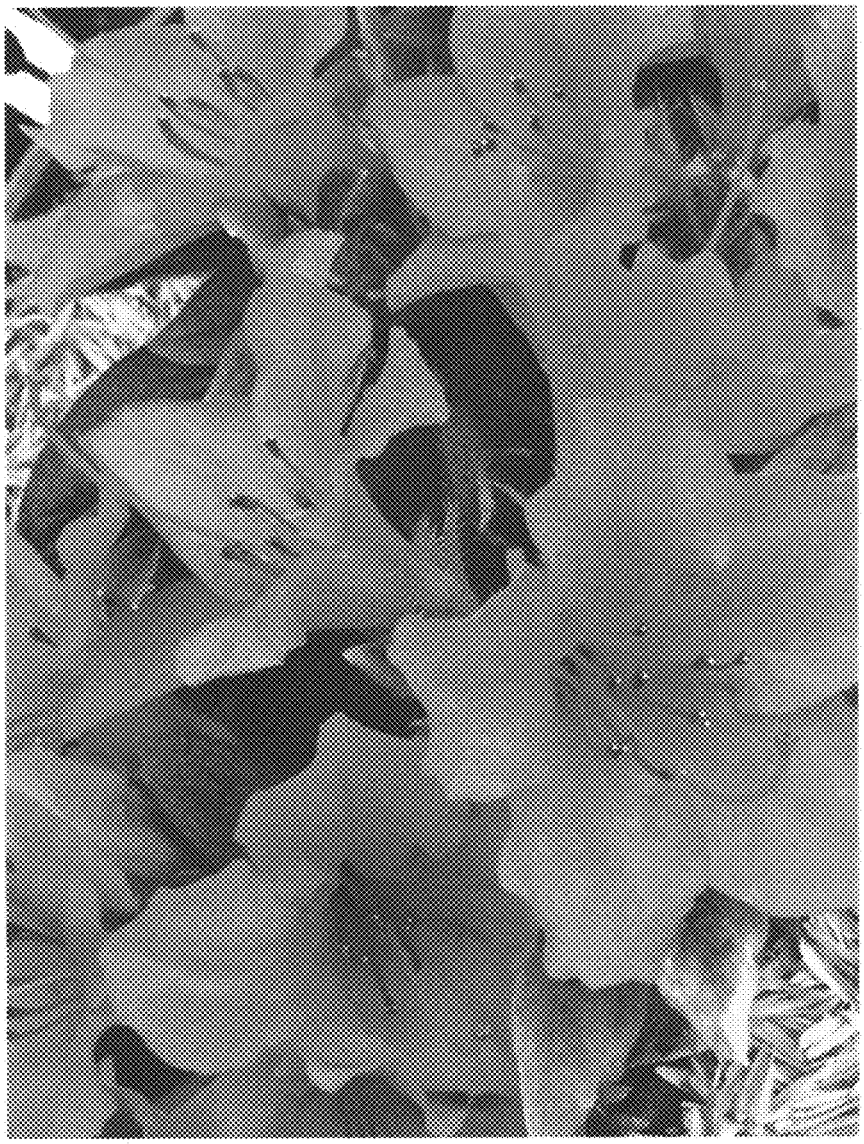
FIG. 1 illustrates fully expanded trusses with bright red/orange flowers; image taken from a 2-year-old container plant grown in Grand Haven, Mich., in 2020.
Figure 2:
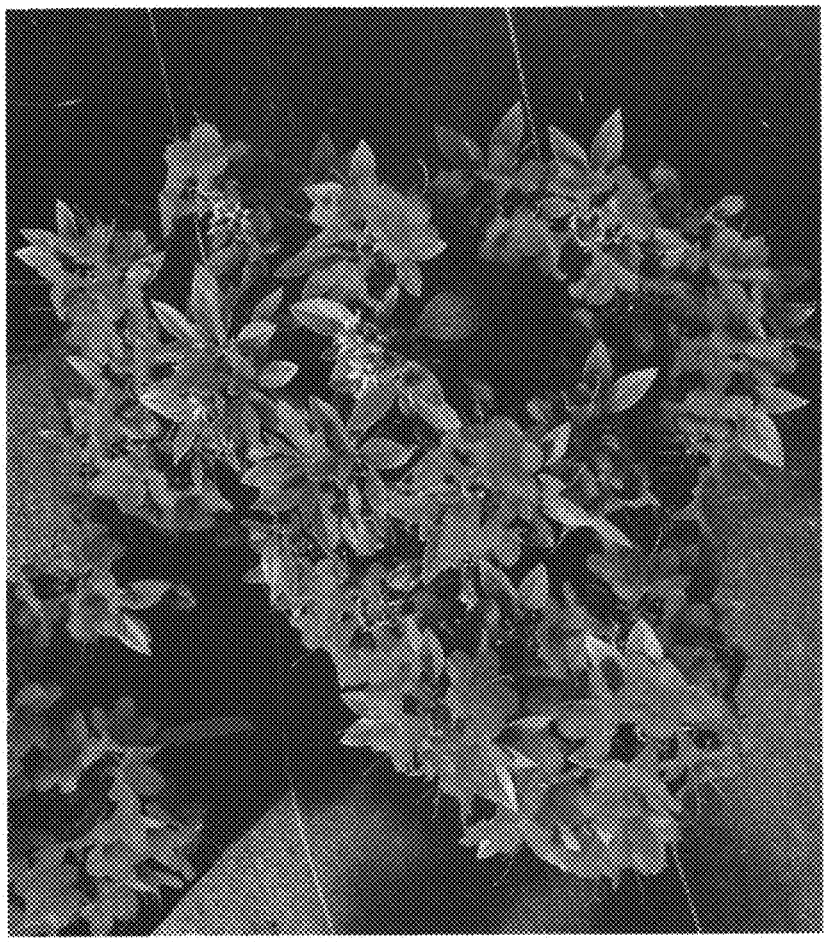
FIG. 2 illustrates the compact plant habit, plant form and profusion of flowers on a 2-year-old container-grown plant in Grand Haven, Mich., in 2020.

The following is a detailed description of the botanical characteristics of the new and distinct hybrid evergreen azalea known by the denomination 'NCRX6'. The detailed description was taken on a 3-year-old container-grown plant in Mills River, N.C., in 2020. Where pertinent, descriptive data was supplemented by observations/measurements taken on a 5-year-old individual located in field trials in Mills River, N.C., as well as information provided from cooperators in Grand Haven, Mich. All colors cited herein refer to The Royal Horticultural Society Colour Chart (The Royal Horticultural Society (R.H.S.), London, 2015 Edition. Where specific dimensions, sizes, colors, and other characteristics are given, it is to be understood that such characteristics are approximations or averages set forth as accurately as is practicable.

PLANT

Plant type: Evergreen azalea.
Growth habit/form: Globose, upward arching.
Height at maturity: 75 cm-100 cm.
Width at maturity: 100 cm -120 cm.
Roots: Fibrous. Tan, not accurately measured with R.H.S. chart.
Growth rate: Moderate.
Shoots and branches:

*Shoots* (*current years softwood new growth*).—Shape: Rounded. Color: RHS Yellow-Green Group 147D. Texture: Pubescent. Pubescence color: RHS Greyed-Orange Group N165B. Shoot diameter: 1.5 mm to 3 mm. Shoot length: Variable, ranging from about 7 cm to 15 cm.

*Shoots* (*prior years woody shoot*).—Shape: Rounded. Color: RHS Greyed-Orange Group 165A, with exfoliating streaks of RHS Greyed-Orange Group 165B. Texture: Exfoliating, some pubescence. Pubescence color: RHS Greyed-Orange Group 164B. Stem diameter: Generally 2.5-5.5 mm. Stem length: Variable, ranging from 5-20 cm. Stem aspect: 0-90°.

*Branches* (*mature woody branches*).—Shape: Rounded. Color: RHS Greyed-Orange Group 177B, exfoliating streaks of RHS Greyed-Orange Group 164A. Texture: Gently exfoliating. Branch diameter: Approximately 5 mm to 10 mm. Branch length: Variable, approximately 20-50 cm. Branching: Freely-branched. Number of lateral branches: Variable, 30-50.

FOLIAGE

Type: Evergreen.
Arrangement: Alternate.
Division: Simple.
Shape: Elliptic to obelliptic.
Apex: Mucronate.
Base: Cuneate.
Margin: Entire, ciliate.
Venation: Reticulate.
Internode length: Approximately 5 mm to 15 mm.
Immature leaf:

*Adaxial* (*upper*) *surface.*—
*Color.*—RHS Yellow-Green Group 144A.
*Surface.*—Pubescent.
*Pubescence color.*—RHS White Group N155B.

*Abaxial (lower) surface.*—
*Color.*—RHS Green Group 143C.
*Surface.*—Pubescent.
*Pubescence.*—RHS White Group N155B.

Mature leaf:
*Length.*—Approximately 2-5 cm.
*Width.*—Approximately 1.5-3 cm.
*Color.*—Adaxial (upper) surface: RHS Green Group 139A. Abaxial (lower) surface: RHS Green Group N138B. Surface: Both sides are lightly pubescent along the midrib. Pubescence color: RHS Greyed-Orange Group 163C. Fall/Winter Color (Leaf): Adaxial side: RHS Yellow-Green Group 147A. Abaxial side: RHS Yellow-Green Group 148B.
*Leaf attachment.*—Petiolate.

Petiole:
*Shape.*—Lunate.
*Length.*—Approximately 6-15 mm.
*Diameter.*—Approximately 1-2 mm.
*Color.*—Adaxial/abaxial side: RHS Yellow-Green Group 144B. Surface: Both sides are pubescent. Pubescence color: RHS Greyed-Orange Group 164B.

FLOWER

Type: Congested terminal raceme (truss).
Flowering season: Mid-Spring (Mid-April to June) reblooms in Early Fall (Late September through October).
Flowering habit: Free-flowering.
Flower number: 2-7 flowers per truss.
Consistency in display: Blooms reliably in the Spring and consistently reblooms in the Fall.
Lastingness of flowers: Each flower lasts approximately 3-7 days.
Fragrance: None.
Self-cleaning or persistent: Self-cleaning.

Truss bud:
*Length.*—Approximately 10-15 mm.
*Diameter.*—Approximately 6-12 mm.
*Bud scales.*—Number: Variable: 5-7. Length: Approximately 10-15 mm. Width: Approximately 6-10 mm. Color prior opening: RHS Yellow-Green Group 145B. Color after flowers emerge: RHS Yellow-Green Group 145B. Texture: Adaxial side is glabrous; abaxial side is pubescent at tip.

Emerging floral buds:
*Shape.*—Elliptic, acuminate.
*Length.*—2.5-4 cm.
*Diameter.*—10-15 mm.
*Color.*—RHS Red Group 43A.

Perianth:
*Diameter at anthesis.*—4.5-6.5 cm.
*Depth.*—2.5-4.5 cm.
*Organization.*—Petals are arranged in a single whorl.
*Aspect.*—Facing upwards and outwards.
*Shape.*—Broadly funnel-shaped.
*Attachment.*—Pedicellate.

Petals:
*Length.*—4-5 cm.
*Width.*—2-3 cm.
*Shape.*—Obovate.
*Apex.*—Obtuse.
*Base.*—Acuminate.
*Margin.*—Undulate.
*Fused or unfused.*—Fused at the midpoint.
*Color.*—Color is consistent from opening to anthesis. Adaxial (upper) surface: RHS Red Group 43A. Blotch: RHS Red Group 46A. Surface: Smooth, silky. Abaxial (lower) surface: RHS Red Group 43A. Surface: Smooth, silky.
*Petal number.*—5.

Calyx/receptacle:
*Shape.*—Star-shaped, single-whorl of persistent sepals.
*Sepals.*—Number: 5. Length: 8-11 mm. Width: 3-5 mm. Shape: Lanceolate. Apex: Acuminate. Margin: Entire, ciliate. Fused or unfused: Unfused. Color: RHS Yellow-Green Group 145B. Surface: Adaxial side is glabrous; abaxial side is pubescent.

Pedicels:
*Shape.*—Rounded.
*Length.*—11-16 mm.
*Diameter.*—1-2 mm.
*Color.*—RHS Red Group 44A.
*Surface.*—Both sides are pubescent.

REPRODUCTIVE ORGANS

Generally, flowers are both complete and perfect, although individual flowers may vary.

Gynoecium:
*Pistil number.*—1.
*Pistil length.*—5-7 cm.
*Stigma shape.*—Orbicular to elliptic.
*Stigma length.*—1.5-2 mm.
*Stigma width.*—1.5-2 mm.
*Stigma color.*—RHS Red Group 43C.
*Style length.*—5-6 cm.
*Style diameter.*—0.5-1 mm.
*Style color.*—RHS Red Group 43C.
*Ovary shape.*—Dome-shaped.
*Ovary length.*—4-6 mm.
*Ovary diameter.*—2-4 mm.
*Ovary color.*—RHS Yellow-Green Group 147B.
*Surface.*—Tomentose, RHS White Group 155A.

Androecium:
*Stamen number.*—7.
*Anther shape.*—Ovoid with two apical pores.
*Anther attachment.*—Dorsifixed.
*Anther length.*—2-4 mm.
*Anther width.*—1-2 mm.
*Anther color.*—RHS Red-Purple Group 59A.
*Filament length.*—3-5 cm.
*Filament diameter.*—Approximately 1 mm.
*Filament color.*—RHS Red Group 43C.
*Amount of pollen.*—Moderate.
*Pollen type.*—Vicinate.
*Pollen color.*—RHS Yellow-White Group 158B.

OTHER CHARACTERISTICS

Fruit type: Capsule.
Fruit texture: Pubescent/tomentose.
Fruit length: Approximately 10 mm if successfully pollinated, ~5 mm if not.
Fruit diameter: Approximately 5 mm if successfully pollinated, ~2.5 mm if not.

Fruit color:
*Immature.*—RHS Yellow-Green Group 147B.
*Mature.*—RHS Greyed-Orange Group 177A/B.

Seed number: Variable 0 to hundreds, although fruit set is rare.

Seed length: Approximately 1.5 mm.

Seed diameter: Approximately 1 mm.

Seed color: RHS Yellow-Orange Group 22B.

Propagation: Roots readily (>90%) from firm, terminal, softwood stem cuttings taken in mid-summer. 'NCRX6' roots well when the bottom 2 cm of the stems are treated for 5 seconds with 3,000-5,000 ppm of potassium salt of indole-3-butyric acid (KIBA) dissolved in water and placed under intermittent mist for 8-10 weeks until roots form.

Disease and insect resistance: No significant disease or insect pests have been observed.

Cold hardiness: Has been reliably cold hardy in USDA 6b. Has not been evaluated in colder regions.

Ploidy: 'NCRX6' is a stable tetraploid. 'NCRX6' has been confirmed via flow cytometry and remains stable after successive propagation.

What is claimed is:

1. A new and distinct cultivar of *Rhododendron* plant named 'NCRX6' as herein illustrated and described.

* * * * *